(12) United States Patent
Wallin et al.

(10) Patent No.: US 11,802,832 B2
(45) Date of Patent: Oct. 31, 2023

(54) METHOD AND SYSTEM FOR DETERMINING A CONTENT OF $H_2S$

(71) Applicant: Opsis AB, Furulund (SE)

(72) Inventors: Svante Wallin, Bjärred (SE); Leif Uneus, Höllviken (SE)

(73) Assignee: Opsis AB, Furulund (SE)

( * ) Notice: Subject to any disclaimer, the term of this patent is extended or adjusted under 35 U.S.C. 154(b) by 380 days.

(21) Appl. No.: 16/612,332

(22) PCT Filed: Apr. 17, 2018

(86) PCT No.: PCT/EP2018/059762
§ 371 (c)(1),
(2) Date: Nov. 8, 2019

(87) PCT Pub. No.: WO2018/206243
PCT Pub. Date: Nov. 15, 2018

(65) Prior Publication Data
US 2020/0173913 A1    Jun. 4, 2020

(30) Foreign Application Priority Data
May 10, 2017 (SE) .................................. 1750576-9

(51) Int. Cl.
*G01N 21/75* (2006.01)
*G01N 21/33* (2006.01)
(Continued)

(52) U.S. Cl.
CPC ............ *G01N 21/33* (2013.01); *G01N 21/75* (2013.01); *G01N 33/0013* (2013.01); *G01N 33/0044* (2013.01); *G01N 2021/0193* (2013.01)

(58) Field of Classification Search
CPC .... G01N 21/75; G01N 21/33; G01N 33/0044; G01N 33/00134
(Continued)

(56) References Cited

U.S. PATENT DOCUMENTS

| | | | |
|---|---|---|---|
| 3,300,282 A | 1/1967 | Risk et al. | |
| 3,969,626 A * | 7/1976 | Saltzman | G01N 21/33 |
| | | | 250/343 |

(Continued)

FOREIGN PATENT DOCUMENTS

| | | |
|---|---|---|
| CA | 2768359 C | 8/2013 |
| GB | 769997 | 3/1957 |
| JP | H11118676 | 4/1999 |

OTHER PUBLICATIONS

Melsheimer, J. et al, Journal of the Chemical Society Faraday Transactions 1992, 88, 2101-2108.*
(Continued)

*Primary Examiner* — Arlen Soderquist
(74) *Attorney, Agent, or Firm* — Hodgson Russ LLP

(57) ABSTRACT

The present invention relates to a method (1) for determining a content of $H_2S$ in a process gas comprising $H_2S$. The method (1) comprises extracting (2) a sample of the process gas, performing oxidation (4) of at least a major portion of $H_2S$ of the sample, whereby oxidation products comprising elemental sulfur are formed, analysing (6) the oxidized sample by optical absorption spectroscopy at wavelengths above 310 nm, and determining (8) the content of $H_2S$ in the process gas based on the analysing. The invention further relates to a system (100) for determining a content of $H_2S$ in a process gas comprising $H_2S$, and use of system (100).

10 Claims, 4 Drawing Sheets

(51) Int. Cl.
G01N 33/00 (2006.01)
G01N 21/01 (2006.01)

(58) Field of Classification Search
USPC .......................................................... 436/121
See application file for complete search history.

(56) References Cited

U.S. PATENT DOCUMENTS

| | | | |
|---|---|---|---|
| 4,678,756 | A | 7/1987 | Parks |
| 5,547,649 | A * | 8/1996 | Beck .................. B01D 53/8612 423/230 |
| 5,739,038 | A | 4/1998 | Burrows |
| 6,319,722 | B1 | 11/2001 | Litwin et al. |
| 6,355,150 | B1 | 3/2002 | Savin-Poncet et al. |
| 8,771,597 | B2 | 7/2014 | Zochbauer et al. |
| 2008/0255769 | A1 | 10/2008 | Zhou et al. |
| 2013/0045541 | A1 | 2/2013 | Fix et al. |
| 2018/0003625 | A1* | 1/2018 | Humblot ................ G01N 21/39 |

OTHER PUBLICATIONS

Melsheimer, J. et al, Berichte der Bunsengesellschaft fur Physikalische Chemie 1997, 101, 726-732.*
Szabo, A. et al., Measuring Science and Technology 2013, 24, paper 065501, 7 pages.*
Brewer, L. et al, Journal of Chemical Physics 1965, 42, 1385-1389.*
Meyer, B. et al, Journal of Physical Chemistry 1972, 76, 2274-2279.*
Hassanzadeh, P. et al, Journal of Physical Chemistry 1992, 96, 6579-6585.*
Olschewski, H. A. et al, Journal of Physical Chemistry 1994, 98, 12964-12967.*
Steudel, R. et al, Topics in Current Chemistry 2003, 230, 117-134.*
Bosch Ojeda, C. et al, Applied Spectroscopy Reviews 2009, 44, 245-265.*
Grosch, H. et al, Journal of Quantitative Spectroscopy & Radiative Transfer 2015, 154, 28-34.*
Fowler, A. et al, Proceedings of the Royal Society of London. Series A 1931, 132, 310-330.*
Lewis, M. N. et al, Physical Review 1939, 55, 894-898.*
Gaydon, A. G. et al, Proceedings of the Royal Society of London. Series A 1947, 189, 313-325.*
Brewer, L. et al, Journal of Chemical Physics 1966, 44, 3274-3278.*
Dagnall, R. M. et al, Analyst 1967, 92, 506-512.*
Syty, A. et al, Applied Optics 1968, 7, 1331-1336.*
Toyoda, M. et al, Bulletin of the Chemical Society of Japan 1974, 47, 95-98.*
Hamouda, A. A. et al, Applied Spectroscopy 1978, 32, 201-204.*
Syty, A., Analytical Chemistry 1979, 51, 911-914.*
Coskun, I. et al, Canadian Iournal of Chemical Engineering 1980, 58, 72-76.*
Saltzman, R. S., Analytica Chimica Acta 1986, 190, 227-233.*
Arowolo, T. A. et al, Analyst 1991, 116, 595-599.*
Van Looij, F. et al, Studies in Surface Science and Catalysisis 1993. 75, 1377-1389.*
Chun, S. W. et al, Applied Catalysis B: Environmental 1998, 16, 235-243.*
Eckert, B. et al, Topics in Current Chemistry 2003, 231, 31-98.*
Dooly, G. et al, IEEE Sensors Journal 2007, 7, 685-691.*
Zagoruiko, A. N. et al, Catalysis in Industry 2010, 2, 343-352.*
Selim, H. et al, Applied Energy 2011, 88, 2601-2611.*
Wang, Y. et al, Industrial & Engineering CHemistry Research 2013, 52, 5616-5625.*
Luo, Q. et al, Advanced Materials Research 2013, 712-715, 688-700.*
Gersen et al., Detection of H2S, SO2 and NO2 in CO2 at pressures ranging from 1-40 bar by using broadband absorption spectroscopy in the UV/VIS range, Energy Procedia, 2014, vol. 63, pp. 2570-2582.
Barshad et al., From Single Component to Multi-Component-UV Analyzers for the Sulfur Recovery Industry, Technical Papers—ISA, 2001, vol. 410, pp. 161-170.
The tail wags the dog, SRU Control, Sulfur, British Sulphur Publishing, May 1995, No. 238, London, GB, pp. 51-60.
Billimers et al., Ultraviolet-Visible Absorption Spectra of Equilibrium Sulfur Vapor: Molar Absorptivity Spectra of S3 and S4, The Journal of Physical Chemistry, 1991, vol. 95, No. 11, pp. 4242-4245.
Tasdemir et al., Selective catalytic oxidation of H2S to elemental sulfur over titanium based Ti—Fe, Ti—Cr and Ti—Zr catalysts. International Journal of Hydrogen Energy, Jul. 2, 2015, vol. 40. pp. 9989-10001.
Eckert et al., Molecular Spectra of Sulfur Molecules and Solid Sulfur Allotropes, Topics in Current Chemistry, 2003, vol. 231, pp. 31-46.

* cited by examiner

METHOD AND SYSTEM FOR DETERMINING A CONTENT OF $H_2S$

TECHNICAL FIELD

The present inventive concept relates to a method for determining a content of $H_2S$ in a process gas comprising $H_2S$, to a corresponding system and a use of the system.

TECHNICAL BACKGROUND

Hydrogen sulfide is a compound with the formula $H_2S$. Hydrogen sulfide is a colourless gas which is poisonous and flammable. Naturally $H_2S$ occurs, for example, in natural gas and in crude petroleum. Due to its inherent disadvantages, it is desired to minimise emissions of $H_2S$, for example in process industry. For this reason, there are legislative limits relating to emissions of $H_2S$. In order to verify that legislative requirements are adhered to and that emissions are minimized, the content of $H_2S$ exiting for instance a chimney or smokestack may need to be monitored. Thus, there is a desire to measure levels of $H_2S$ in various environments.

Frequently, $H_2S$ is found in gas mixtures, for example mixtures including sulfur dioxide, $SO_2$. It is a problem to measure levels of $H_2S$ in gas mixture due to UV absorption being a broad continuous absorption without peaks and IR absorption suffer from interference from $H_2O$ and other gaseous compounds. For example, $SO_2$ and other compounds masks or interferes with $H_2S$ in optical absorption spectrometry measurements.

It is known to measure $H_2S$ levels in exhaust gas mixtures including $SO_2$ by first treating the gas mixture in a so called scrubbing procedure to remove $SO_2$ from the gas mixture, followed by conversion of $H_2S$ to $SO_2$, after which measurements are made on $SO_2$. The scrubbing procedure is problematic, for example due to a corrosive environment in the scrubber. Scrubbing material is typically consumed during the scrubbing procedure, thus, requiring maintenance and replacement. Further, if the scrubbing procedure does not perform as desired, measurement of $H_2S$ will be erroneous. In addition, optical detection of $SO_2$ may be problematic due to interferences from other compounds.

There is, thus, a need for efficient measurement of $H_2S$ and especially efficient measurements of $H_2S$ in gas mixtures, without disadvantages of prior art.

SUMMARY OF THE INVENTION

It is an object of the present inventive concept to overcome the above problems, and to provide an improved method for determining a content of $H_2S$ in a process gas comprising $H_2S$.

The present inventive takes advantage of the realization that $H_2S$ of process gas efficiently may be converted into compounds which are detectable at wavelengths where less interference from other compounds occurs. There is, thus, no need for cleaning the process gas from interfering compounds, by e.g. scrubbing the process gas.

According to a first aspect, this and other objects are achieved by a method for determining a content of $H_2S$ in a process gas comprising $H_2S$. The method comprises extracting a sample of the process gas, performing oxidation of at least a major portion of $H_2S$ of the sample, whereby oxidation products comprising elemental sulfur are formed, analysing the oxidized sample by optical absorption spectroscopy at wavelengths above 310 nm, and determining the content of $H_2S$ in the process gas based on the analysing.

Extracting a sample from the process gas is efficient for obtaining a manageable and efficient sample volume or flow of sample for further treatment and analysis.

Oxidation of at least a major portion of $H_2S$ of the sample efficiently converts $H_2S$ into compounds or oxidation products with properties, including light absorption properties, differing from those of $H_2S$. The so formed oxidation products comprise elemental sulfur.

Analysing the oxidized sample by optical absorption spectroscopy at wavelengths above 310 nm may efficiently counteract undesired detection interference from compounds not related to the presence of $H_2S$ in the sample. The combination of oxidizing at least a major portion of $H_2S$ in the sample to oxidation products comprising elemental sulfur, and detection at wave lengths above 310 nm, provides for efficient detection and determination of compounds correlating to presence of $H_2S$ in the sample. It is to be noted that the analysing the oxidized sample is according to the present inventive concept performed subsequent to the performing oxidation of at least a major portion of $H_2S$ of the sample.

Determining the content of $H_2S$ in the process gas based on the analysing, is an efficient means for determining the content of $H_2S$ in the process sample.

It should be noted that within the context of this application the term "content of $H_2S$" may relate to any suitable way of expressing the presence of $H_2S$ in a gas. A content of $H_2S$ may, for example, be expressed as the concentration of $H_2S$ in a volume such as a number of moles or a mass unit per volume unit, or it may be expressed as a total number of moles or mass present.

It should further be noted that the term "process gas" may refer to any type of gas used in or produced by any industrial process, including exhaust gas or flue gas, as well as gases originating from extraction or refing of compounds, such as crude oil.

The analysing the oxidized sample by optical absorption spectroscopy may comprise obtaining at least one spectrum, and determining the content of $H_2S$ in the process gas based on the analysing may comprise comparing the obtained at least one spectrum with at least one reference spectrum or data.

The analysing the oxidized sample by optical absorption spectroscopy may be at wavelengths between 310 and 700 nm, preferably between 310 and 500 nm, and more preferably between 320 and 360 nm. The specified ranges may also include the upper and lower limits of the ranges.

It is realised that although wavelengths above 310 nm are used for the analysing and the determining the content of $H_2S$, the optical absorption spectroscopy may operate or detect light also below 310 nm in wavelength.

The analysing the oxidized sample by optical absorption spectroscopy may be at wavelengths of 320 nm and above.

The analysing the oxidized sample by optical absorption spectroscopy may be at wavelengths between 320 and 360 nm, which is advantageous in that a relatively speaking quick analysis may be performed.

The determining the content of $H_2S$ in the process gas based on the analysing, may comprise comparing with an analysis of a sample with known amount or content of $H_2S$.

Comparing with a reference spectrum allows efficient determination of a content of $H_2S$ in the process gas also in situations where the oxidation products are unknown and/or the conversion ratio of $H_2S$ in the oxidation is not known.

The reference spectrum may be obtained using oxidation and analysing parameters and equipment mimicking or being identical to the oxidation and analysis of the sample of process gas.

Results and/or data from the analysing the oxidized sample by optical absorption spectroscopy may be compared with results and/or data from a reference analysis or analysis of sample comprising a known content or concentration of $H_2S$, in any suitable way. Reference or calibration data or calibration curves may be used in comparison. Determination using standard addition(s) may further be used. Any suitable way of comparing data from the analysis of $H_2S$ in the process gas, with known or reference data may be used. Selected data from spectra may be used, such as, for example, intensities, peak heights or peak areas of spectra may be used. The concentration of a particular species or compound may be calculated from the Beer-Lambert law based on a known absorption cross section of the species is question and a known absorption length.

It is realised that comparing the obtained at least one spectrum with at least one reference spectrum, may comprise comparing data from the spectra in any suitable way to determine the content of $H_2S$. Data or information from the optical measurements may, for example, be compared without graphical illustrations of spectra. Data from specific wavelength intervals or specific distinct wavelengths may be compared.

It is realised that if it is established or known which reaction product(s) are formed from the oxidation reaction(s), optionally together with the degree of conversion of $H_2S$, embodiments may be realised with efficient determination of content of $H_2S$ without comparing with a reference spectrum.

The performing oxidation may comprise contacting $H_2S$ of the sample with an oxidizing agent. Thus, efficient oxidation may be realized.

The performing oxidation may further comprise heat treating the sample. Thus, efficiency of oxidation may be increased.

The heat treating the sample may be at a temperature of 300° C. or above, preferably at 300° C. to 400° C., most preferably at 300° C. to 310° C., such as 305° C. At those temperatures efficiency of oxidation may be increased.

The performing oxidation may be catalysed by activated aluminium(III) or titanium(IV) oxide. Such catalysts may increase efficiency of oxidation.

$S_2$ may be formed during the performing oxidation. The oxidation products may comprise $S_2$.

Oxidation of $H_2S$ may produce sulfuric compounds having the formula $S_2$.

$S_2$ may react further under formation of elemental sulfur, comprising, for example $S_8$.

It is to be understood that the oxidation of $H_2S$ may directly form oxidation products which may be detected in the analysis, and in addition the oxidation products may in turn be converted to compounds which are detected in the analysis. For example, $S_2$ may be formed in the oxidation, which $S_2$ in turn may be converted to $S_8$, which in turn, may be converted to for example other forms of elemental sulfur.

Thus, compounds detected in the analysis step may be selected from the group consisting of oxidation products from the oxidation, and compounds obtained from further reaction of oxidation products, and combinations thereof.

Compounds detected in the analysis step may be selected from the group consisting of $S_2$, $S_8$, and all other forms of elemental sulfur.

Elemental sulfur may be formed during the performing oxidation.

The oxidation products may have absorption maxima above 310 nm.

The oxidation products may have absorption maxima above 320 nm.

The analysing the oxidized sample by optical absorption spectroscopy may be performed at or above 150° C., preferably between 170° C. and 190° C.

The optical absorption spectroscopy may comprise use of light emitted from a broad band Xenon light source. The light may include UV light.

Light from a Xenon light source including UV light may assist in converting oxidation products to other products or compounds.

The oxidizing agent may be present in the process gas or may be introduced to the sample after the extracting.

There may be sufficient oxidizing agents in the process gas in order to oxidize $H_2S$ in the sample. Additional oxidizing agent may be introduced for the oxidation of $H_2S$.

As used herein, an oxidizing agent is an agent which is capable of oxidizing $H_2S$ in the sample under the circumstances present during oxidation.

A sufficient or surplus of oxidizing agents at levels being at level with or surpassing those necessary to oxidize all of $H_2S$ in the sample may be present during oxidation.

Oxidizing agent may be present during oxidation at such amounts or concentrations in order to oxidize at least a major portion of the $H_2S$.

The oxidizing agent may be oxygen and/or $SO_2$.

The optical absorption spectroscopy may be differential optical absorption spectroscopy, DOAS.

DOAS may result in efficient analysis of the $H_2S$ content of the process gas.

The sample may be extracted as a flow of gas from a flow of process gas.

Such extraction may allow for efficient sampling and determining the content of $H_2S$ in the process gas. Further, continuous monitoring or determining the content of $H_2S$ in the process gas may be realized.

It will be appreciated that the sampling may be performed by continuous sampling, or as a flow during a limited interval of time.

The sample may be extracted as a flow of gas from a flow of flue gas in a smokestack.

According to an aspect of the present invention, there is provided a system for determining a content of $H_2S$ in a process gas comprising $H_2S$, the system comprising: an extractor arranged to extract a sample of the process gas, a reactor arranged for oxidation of at least a major portion of $H_2S$ of the sample, whereby oxidation products comprising elemental sulfur are formed, an optical absorption spectrometer arranged to analyse the oxidized sample at wavelengths above 310 nm, and to output data pertaining to the analysis, and a processing unit arranged to receive the data from the optical absorption spectrometer and to determine the content of $H_2S$ in the process based on the data.

It should be noted that the inventive system may incorporate any of the features described above in association with the inventive method, and has the same corresponding advantages.

The extractor may be further arranged to extract the sample as a flow of gas from a flow of process gas in a smokestack.

The optical absorption spectrometer may be a differential optical absorption spectrometer.

According to another aspect of the present invention, there is provided a use of the system.

It is noted that the disclosure relates to all possible combinations of features recited in the claims.

BRIEF DESCRIPTION OF THE DRAWINGS

This and other aspects of the present disclosure will now be described in more detail, with reference to the appended drawings showing embodiments of the invention, in which.

As illustrated in the figures, the sizes of parts and portions for example may be exaggerated for illustrative purposes and, thus, are provided to illustrate the general structures of embodiments of the present invention. Like reference numerals refer to like elements throughout.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

Figure 1:
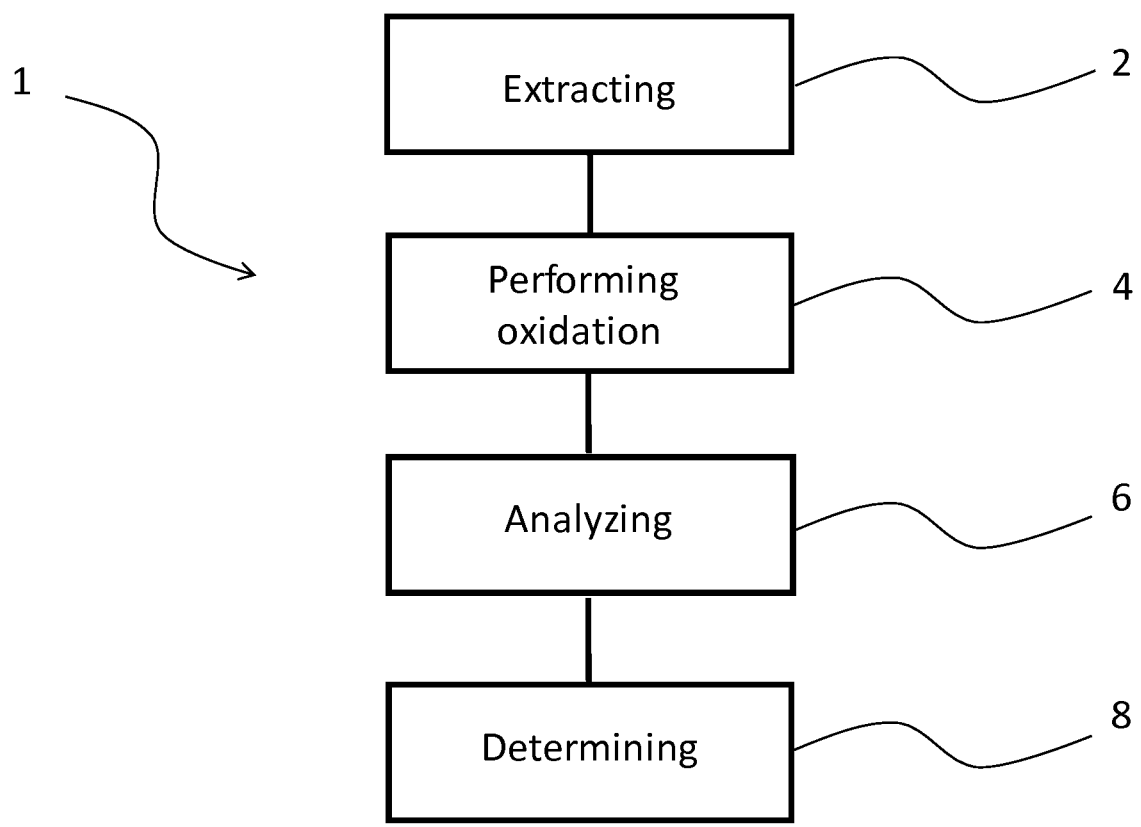
FIG. 1 schematically illustrates a method for determining a content of $H_2S$ in a process gas comprising $H_2S$.

An embodiment will now be described with reference to FIG. 1. FIG. 1 schematically illustrates a method 1 for determining a content of $H_2S$ in a process gas comprising $H_2S$. The method 1 comprises extracting 2 a sample of the process gas; performing oxidation 4 of at least a major portion of $H_2S$ of the sample, whereby oxidation products comprising elemental sulfur are formed, analysing 6 the oxidized sample by optical absorption spectroscopy at wavelengths above 310 nm, and determining 8 the content of $H_2S$ in the process gas based on the analysing.

Figure 2:
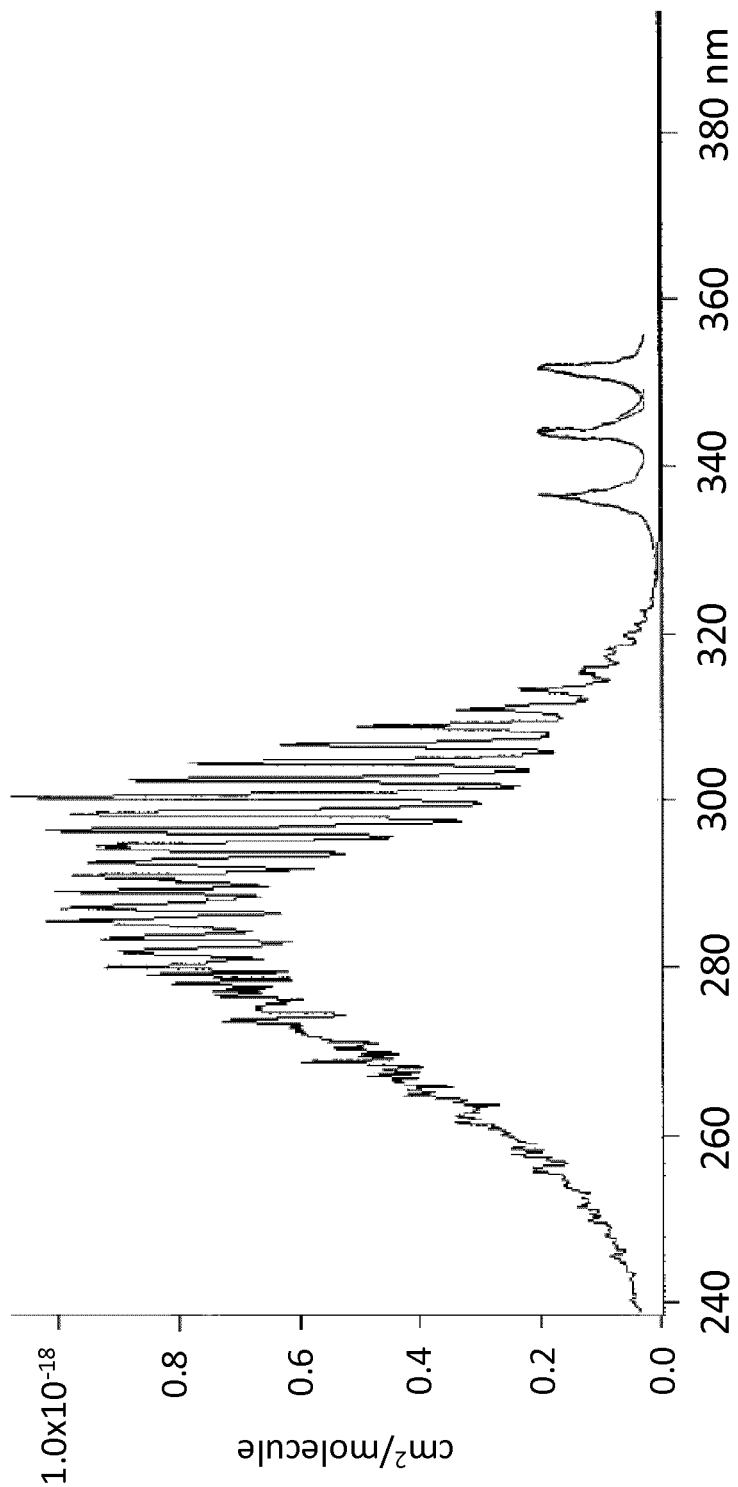
FIG. 2 schematically illustrates a spectrum obtained according to an embodiment.

The method 1 efficiently allows the content of $H_2S$ in process gas to be determined, at least in part since the method allows for minimizing detection interference from compounds which are not derived from $H_2S$. FIG. 2 illustrates a spectrum obtained from analysis of process gas containing $H_2S$, where a sample has been extracted and oxidized similarly to embodiments. The analysis involved optical absorption spectroscopy on the oxidized sample at wavelengths approximately between 240 and 355 nm. It is evident from the spectrum that between 240 and 310 nm considerable absorption occurs, in part by $SO_2$. It shall be mentioned that $H_2S$ has absorbance within the interval 240 to 310 nm and would thus be masked by the considerable absorption in this wavelength range. The treatment of the sample by oxidation has resulted in oxidation products from $H_2S$ which is seen as the three peaks within the interval 330 to 360 nm, which peaks are clearly not disturbed by interfering compounds. The three peaks have been identified as corresponding to elemental sulfur compounds.

Performing oxidation of $H_2S$ of the sample will now be discussed. Oxidation of $H_2S$ may, at least in part, be described by what sometimes is referred to as the Claus process, which Claus process describes production of elemental sulfur from gaseous hydrogen sulfide.

An overall reaction describing reactions of the Claus process may be illustrated by reaction (1):

$$8\ H_2S + 5\ O_2 \rightarrow SO_2 + 7/2\ S_2 + 8\ H_2O \qquad (1).$$

Oxidation of $H_2S$ may, at least in part, further be described by reaction (2):

$$2\ H_2S + SO_2 \rightarrow 3\ S + 2\ H_2O \qquad (2).$$

Reaction (2) may be catalysed by a suitable catalyst, for example activated aluminium(III) or titanium(IV) oxide. $SO_2$ acts as oxidizing agent in reaction 2.

The elemental sulfur obtained in anyone of reactions (1) and (2) may be converted to other forms of elemental sulfur or other sulfur compounds.

The oxidation may be described by anyone of reactions (1) and (2) and combinations of both.

Elemental sulfur formed in the oxidation of $H_2S$ may transform to other sulfur compounds or forms of elemental sulfur. Such transformation may be assisted by light emitted during the optical absorption spectrometry, for example if a Xenon lamp is used during the spectrometry. Particularly, UV light will assist in the transformation.

The use of the invention and embodiments of the invention for determining a content of $H_2S$ in a process gas comprising $H_2S$ comprises performing oxidation of $H_2S$, according to discussions herein. Any suitable type of process gas may be relevant. The oxidation of $H_2S$, for example as illustrated by reactions (1) and/or (2) may be realized by compounds acting as oxidizing agents being present in the process gas, and/or may be realized by compounds added to the sample of process gas, depending on the type of process gas. Typically, the process gas comprises small amounts of $H_2S$ and, thus, only small amounts of oxidizing agent(s) are necessary for oxidation. Small amounts of oxidizing agent(s) may be present as for example $O_2$ and/or $SO_2$. If a user of the method is uncertain with regard to if a sufficient amount of oxidizing agent is present or not, the method according to an embodiment may be performed without addition of oxidizing agent and the results analysed to find out if oxidation of $H_2S$ occurs, optionally by comparing with performance with addition of oxidizing gas.

For example, if the process gas is a flue gas, the process gas may comprise $SO_2$. For example, if the process gas is a gas flow from or within a paper mill, or as a mixture with air the process gas may contain $SO_2$ and/or $O_2$.

The method may be performed with an addition of oxidizing agent. Addition of oxidizing agent may be based on an expected or estimated amount of $H_2S$ in the process gas.

Addition of oxidizing agent may be in excess in relation to the amount of $H_2S$. It is not necessary to estimate the amount of $H_2S$ in the process gas.

Figure 3:
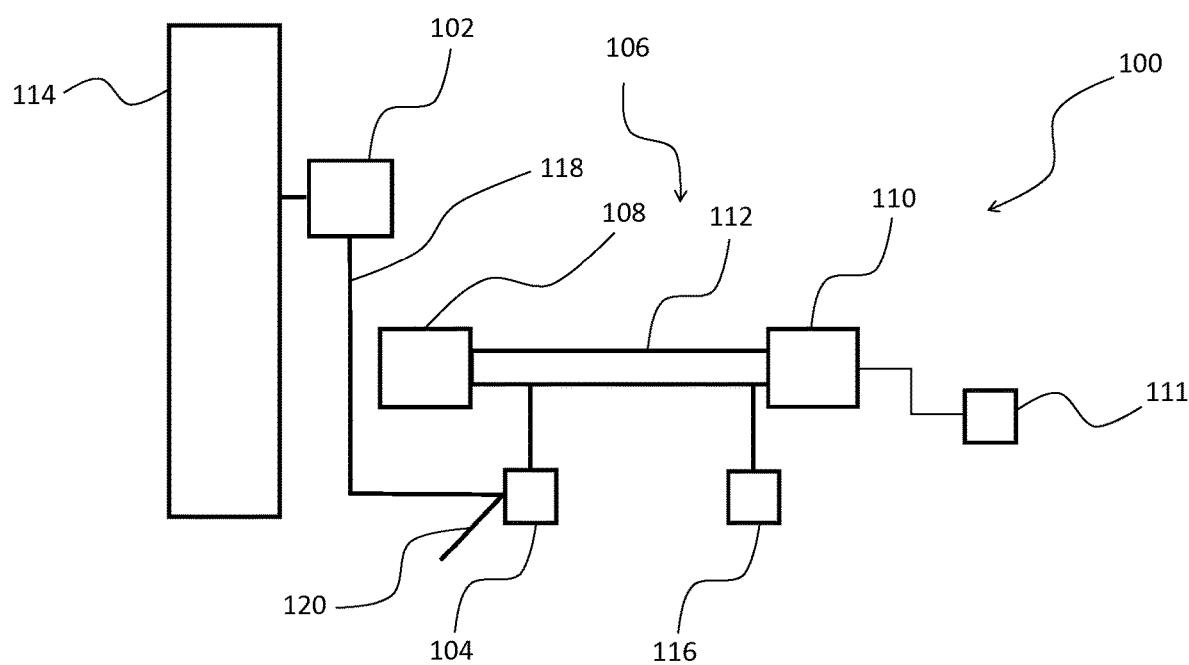
FIG. 3 schematically illustrates a system according to embodiments.

With reference to FIG. 3, a method and a system for determining a content of $H_2S$ in a process gas comprising $H_2S$ will now be discussed. FIG. 3 illustrates a system 100 for determining a content of $H_2S$ in a process gas comprising $H_2S$. The system 100 comprises: an extractor 102 arranged to extract a sample of the process gas, a reactor 104 arranged for oxidation of at least a major portion of $H_2S$ of the sample, whereby oxidation products are formed, an optical absorption spectrometer 106 arranged to analyse the sample above 310 nm and to output data pertaining to the analysis, and a processing unit 111 arranged to receive the data from the optical absorption spectrometer 106 and to determine the content of $H_2S$ in the process gas based on the data.

As further illustrated in FIG. 3, the optical absorption spectrometer 106 may comprise a light emitter 108, which may be arranged to emit broad spectral light comprising light above 310 nm in wavelength. The optical absorption spectrometer 106 further may comprise a light receiver 110, which is arranged to receive and register or convey light emitted from the light emitter 108 after having passed through an absorption device 112. The absorption device 112 is in the depicted embodiment of FIG. 3 a duct through which the sample gas may be conveyed. The optical absorption spectrometer 106 of FIG. 3, comprises a spectrometer, not shown, for analysing the light having passed through the absorption device 112. The spectrometer may be connected to the light receiver 110 in different ways. The spectrometer may be arranged adjacent to or directly on the light receiver 110. The spectrometer may as an alternative be arranged at a distance from the light receiver 110. In this case light as received by the light receiver 110 may by conveyed or forwarded to the spectrometer through an optical fibre, not shown. The spectrometer may be of any suitable type. The spectrometer may preferably include analysing capabilities used to analyse the light received by the light receiver 110. The spectrometer of the optical absorption spectrometer 106 may produce and output data pertaining to the analysis of the light being carried out. The optical absorption spectrometer 106 of FIG. 3 is connected to the processing unit 111.

According to this example, the sample of process gas is obtained from a stack 114. The reactor 104 may comprise an inlet for oxidizing agent for oxidation of at least a major part of $H_2S$ in the sample. According to an embodiment, at least a part of the system is arranged internally in a stack or pipe arranged for forwarding process gas.

With further reference to FIG. 3 a method 1 for determining a content of $H_2S$ in a process gas comprising $H_2S$ will now be discussed in detail as an exemplary method and with reference to the system also discussed with reference to FIG. 3 where relevant. Suitable pipings may be employed for passing of gas through the system, where relevant. The process gas 102 may be gas from a stack emitting gaseous exhausts from a petroleum industry. A sample is extracted from the process gas. The extracting 2 according to this example is by means of continuous pumping a gas flow from the stack 114 using pump 116 and pipings 118. It is realized that samples alternatively may be provided, for example, batch wise, or as distinct sample volumes. In other applications, for example a pressure differences between the stack and its surrounding may be used instead of a pump 116. The, thus, collected sample is forwarded via pipings 118 to the reactor 104, which may be of any suitable shape and material and according to this example is a vessel made of metal. The reactor 104 of this example contains a catalyst for oxidation of $H_2S$. In this example, the sample is heated by a heater (not illustrated) such that it is maintained above 300° C., and around 305° C., in the reactor 104. The process gas of this example contains sufficient amount of oxidizing gas to oxidise at least a major part of the $H_2S$. With other process gasses or examples, oxidizing agent(s) may be needed. Oxidizing agents may be added via a duct 120 suitably connected to or upstream the reactor 104. Therefore, the reactor may be arranged to receive oxidizing agent(s), for example oxygen, air, or any other suitable oxidizing agent. In the reactor 104, $H_2S$ of the sample is contacted with oxidizing agents and at least a major part of the $H_2S$ is oxidized. According to this example, essentially all of the $H_2S$ present in the sample is oxidized. The oxidation results in oxidation products, for example according to anyone of the reactions (1) and (2). The oxidation products may be, for example, elemental sulfur such as $S_2$. After performing the oxidation 4 the sample is forwarded for sample analysis by absorption spectroscopy, taking place in the optical absorption spectrometer 106, whereby continuous light comprising wavelengths in the range of 240 to 360 nm is passed through the sample. The light receiver 110 detects, and processes, light having passed through the sample. A spectrum, similar to the spectrum illustrated in FIG. 2 is obtained from the sample analysis by the spectrometer of the optical absorption spectrometer 106. Compounds in the sample may absorb light within the emitted light range as is known to a skilled person. As described above a spectrometer is typically used for determination of the spectrum of the radiation after absorption in the absorption device 112. The measured spectrum is analysed and/or compared to a known spectrum of the radiation source and the unique absorption spectra for the gas species along the radiation path may thus be identified. It is known that the absorption of light by a compound is proportional to the concentration of the compound and the pass length of the light through the sample containing the compounds. Reference may be made, for example, to Beer's law in this respect. According the Beer-Lambert law the absorption for a specific compound or species may be calculated as follows: $A=\ln(I_0/I_1)=\varepsilon \cdot L \cdot c$, where $\varepsilon$ is absorption cross section of the species is question, L is the absorbing length and c is the concentration of the species. Hence, by knowing the length L of the absorption device 112 and the absorption cross section $\varepsilon$ of the species in question, the concentration c of the species may be calculated. The calculation may thus be performed by the processing unit 111, based on the data received form the optical absorption spectrometer 106 in combination with known data pertaining to known cross sections $\varepsilon$ for species of interest. In this example, the cross section of sulfur comprising oxidation products originating from the $H_2S$ are typically of interest as this allows for determination of the content or concentration of $H_2S$ in the process gas being extracted from the stack 114.

After the sample analysis, the sample of process gas may be returned back to the flow of process gas or elsewhere.

Determining 8 the content of $H_2S$ in the process gas is in this example made by comparing absorption data obtained from the analysis with data obtained from a reference analysis of a sample with known concentration of $H_2S$ of 1000 ppm, by comparing the spectra. Sample with other known concentrations of $H_2S$ may be used similarly. Peaks in the spectrum above 310 nm from the sample analysis were compared with corresponding peaks from the reference analysis, which enabled quantification of $H_2S$ in the process gas. Several known techniques for quantification of compounds using reference analysis may be used for the determining the content of $H_2S$ in the process gas. It shall be understood from the descriptions herein that it is not necessary to understand which components are formed in the oxidation of $H_2S$ in order to quantify $H_2S$ in the process gas, when taking advantage of reference analysis of a sample with known amount of $H_2S$.

Figure 4:
FIG. 4 schematically illustrates a transmission spectrum obtained during an experiment.

With reference to FIG. 4, determining a content of $H_2S$ in a process gas will now be described with reference to an experiment. In this experiment the process gas consisted of a mixture of $H_2S$ and air. 4 l/min of the process gas was extracted as a sample. The sample was transferred to a reactor 104 wherein the sample was contacted with a catalyst material composed of HASTELLOY® under heating to 300° C. to allow for oxidation of a major portion of the $H_2S$ in the sample to occur under formation of oxidation products comprising elemental sulfur. After the oxidation, the sample was introduced to a one metre absorption device 112, i.e. an optical cell having a length of one metre. An Opsis AR600 DOAS spectrometer was used to record a transmission spectrum, whereby the spectrum illustrated in FIG. 4 was obtained. The transmission spectrum of FIG. 4 is showing a limited part of the recorded spectrum. More specifically, the transmission spectrum of FIG. 4 is showing the transmission in the wavelength interval of 325 nm to 336 nm. The transmission decreases present at about 327 nm, 331 nm and 334 nm correspond to elemental sulfur formed during the oxidation, and, thus, to the content of $H_2S$ in the process gas. The content of $H_2S$ in the process gas may consequently be determined from the transmission decreases in the spectrum. It shall be appreciated that $SO_2$ possibly present in the process gas will not interfere with the transmission decreases corresponding to elemental sulfur, as $SO_2$ has a predominant absorption at wave lengths below those of elemental sulfur. This is evident when comparing with FIG. 2, from which it is clear that $SO_2$ absorbs in a range of 260-320 nm.

The invention claimed is:

1. Method (1) for determining a content of $H_2S$ in a process comprising $H_2S$, the method comprising:
   extracting (2) a sample of the process gas,
   performing oxidation (4) of at least a major portion of $H_2S$ of the sample, wherein the performing oxidation (4) comprises heat treating the sample a temperature of 300° C. to 400° C. in the presence of oxidizing agent and a catalyst, whereby oxidation products comprising elemental sulfur are formed,
   analysing (6) the oxidized sample by optical absorption spectroscopy at wavelengths from 310 nm to 700 nm, and
   determining (8) the content of $H_2S$ in the process gas based on the analysing.

2. The method (1) according to claim 1, wherein
   the analysing (6) the oxidized sample by optical absorption spectroscopy comprises obtaining at least one spectrum, and
   determining (8) the content of $H_2S$ in the process gas based on the analysing comprises comparing the obtained at least one spectrum with at least one reference spectrum.

3. The method (1) according to claim 1, wherein the heat treating the sample is at a temperature of 300° C. to 310° C.

4. The method (1) according to claim 1, wherein the performing oxidation is catalysed by activated aluminium (III) or titanium(IV) oxide.

5. The method (1) according to claim 1, wherein $S_2$ is formed during the performing oxidation.

6. The method (1) according to claim 1, wherein the analysing (6) the oxidized sample by optical absorption spectroscopy is performed at between 170° C. and 190° C.

7. The method (1) according to claim 1, wherein the oxidizing agent is present in the process gas or is introduced to the sample after the extracting of the sample.

8. The method (1) according to claim 1, wherein the oxidizing agent is oxygen.

9. The method (1) according to claim 1, wherein
   the optical absorption spectroscopy is differential optical absorption spectroscopy, DOAS.

10. The method (1) according to claim 1, wherein the sample is extracted as a flow of gas from a flow of process gas.

* * * * *